United States Patent [19]

Knollmueller

[11] 4,357,473
[45] Nov. 2, 1982

[54] METHOD FOR PREPARING ALKOXYSILANE CLUSTER COMPOUNDS; RESULTING NOVEL COMPOUNDS; AND THEIR USE AS FUNCTIONAL FLUIDS

[75] Inventor: Karl O. Knollmueller, Hamden, Conn.

[73] Assignee: Olin Corporation, New Haven, Conn.

[21] Appl. No.: 90,376

[22] Filed: Nov. 1, 1979

[51] Int. Cl.$^3$ .............................. C07F 7/04; C07F 7/18; C09K 5/00
[52] U.S. Cl. ........................... 556/416; 556/417; 556/446; 556/458; 252/78.3
[58] Field of Search ................. 556/416, 417, 446, 458; 252/78.3

[56] References Cited

U.S. PATENT DOCUMENTS

| | | | |
|---|---|---|---|
| 3,965,136 | 6/1976 | Knollmueller | 556/458 X |
| 3,976,675 | 8/1976 | Scott et al. | 556/446 |
| 4,077,993 | 3/1978 | Knollmueller | 556/458 X |

OTHER PUBLICATIONS

Todd et al., "J. Chem. Soc.", 1949, pp. 2637–2640.
"Houben Weyl", vol. VI-2, pp. 108–111, 1963.
George et al., "J. Am. Chem. Soc.", 75, p. 987, 1953.
Peppard et al., "J. Am. Chem. Soc.", 68, p. 73, 1946.
Noll, "Chemistry and Technology of Silicones", Academic Press, N.Y.(1968), p. 82.

*Primary Examiner*—Paul F. Shaver
*Attorney, Agent, or Firm*—William A. Simons; Thomas P. O'Day

[57] ABSTRACT

Described is a process for exchanging some or all of the radicals R' in alkoxysilane cluster compounds with different radicals R''; this process being based on the following reaction:

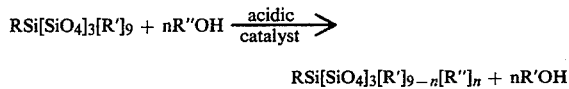

$$RSi[SiO_4]_3[R']_9 + nR''OH \xrightarrow[\text{catalyst}]{\text{acidic}} RSi[SiO_4]_3[R']_{9-n}[R'']_n + nR'OH$$

wherein R is hydrogen, an alkyl, an alkenyl, and an aryl, or an aralkyl; and each R' is independently selected from the same groups as R with the proviso that at least a majority of said R' radicals are sterically hindered alkyl groups having at least 3 carbon atoms; and each R'' is selected from groups consisting of alkyl groups, alkenyl groups, aryl groups, aralkyl groups, functionally substituted alkyl, alkenyl, aryl and aralkyl groups, and polyoxyalkylene groups with the proviso that R'' radicals are different than R' radicals; and n is a number from 1 to 9. Also described are novel alkoxysilane cluster compounds made by this process; these compounds being represented by the following chemical formula:

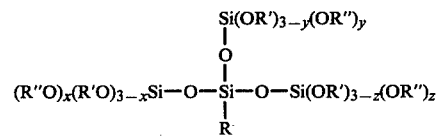

$$(R''O)_x(R'O)_{3-x}Si-O-\underset{\underset{R}{|}}{\overset{\overset{Si(OR')_{3-y}(OR'')_y}{|}}{\underset{|}{O}}}-O-Si(OR')_{3-z}(OR'')_z$$

wherein R, R' and R'' are as defined above, and x, y, and z are individually selected from 0, 1, 2, or 3 with the proviso that the sum of x+y+z is from 1 to 8. Also, described are functional fluid systems (i.e., hydraulic fluid and heat transfer fluid systems) containing these novel alkoxysilane cluster compounds of the above formula.

19 Claims, No Drawings

METHOD FOR PREPARING ALKOXYSILANE CLUSTER COMPOUNDS; RESULTING NOVEL COMPOUNDS; AND THEIR USE AS FUNCTIONAL FLUIDS

BACKGROUND OF THE INVENTION

1. Field of the Invention

The present invention relates to an improved process for making alkoxysilane cluster compounds. Furthermore, the present invention also relates to novel alkoxysilane cluster compounds prepared by this improved process and their use in functional fluid systems.

2. Description of the Prior Art

U.S. Pat. No. 3,965,136, which issued to the present inventor on June 22, 1976, disclosed the preparation of alkoxysilane cluster compounds of the formulae:

$$RSi[OSi(OR')_3]_3 \quad (I)$$

or, written in an other form:

$$RSi[SiO_4]_3[R']_9 \quad (IA)$$

wherein R is hydrogen, an alkyl, alkenyl, aryl or aralkyl, and each R' is independently selected from the same group as R with the proviso that at least a majority of R' radicals are sterically hindered alkyl groups having at least 3 carbon atoms. These alkoxysilane cluster compounds of formulae (I) or (IA) have been disclosed to be very good functional fluids.

In particular, two different processes for preparing these alkoxysilane cluster compounds were disclosed in the forementioned patent. The first method of preparation involves the reaction of a trihalosilane with a trialkoxysilanol in the presence of a hydrogen halide acceptor base. The second disclosed method of preparation involves the reaction of a halosilane with an alkoxysilanol cluster compound in the presence of a base.

An optimization of the above-noted first method of preparation is disclosed in U.S. Pat. No. 4,077,993 which also issued to the present inventor on Mar. 7, 1978. This improved preparation method involves reacting a trihalosilane with a trialkoxysilanol in the presence of a critical amount of acceptor base in a solvent reaction medium while maintaining the reaction temperature in a select range.

It has been found that these methods for preparing alkoxysilane cluster compounds of the formulae (I) or (IA), above, are best suited to those particular compounds where R' is derived from either a secondary or tertiary alcohol. Specifically, it has been found that silanol intermediates HO—Si(OR')$_3$ are more stable when the R' radicals thereof are derived from secondary or tertiary alcohols (e.g., sec-butanol and tert-butanol). And, it has also been found that these more stable intermediates realize greater yields of the desired alkoxysilane cluster product.

In comparison, when the R' groups are sterically hindered alkyls derived from primary alcohols, such as 2-ethylhexanol or 2-ethylbutanol, the preparation of silanols HO—Si(OR')$_3$ is usually more difficult and the yields of these silanols are generally lower. Furthermore, the handling of these silanols with primary R' groups is also difficult because of poor storage stability.

In view of these preparation and handling problems, alkoxysilane cluster compounds with R' being a primary hindered group (i.e., as oppposed to a secondary or tertiary hindered group) have not been made in large commercial quantities. Furthermore, alkoxysilane cluster compounds with R' containing functionalities like fluoro groups, hydroxy groups, and cyano groups are also difficult to prepare and handle when the above-mentioned methods of preparation are employed. Accordingly, a new method for preparing such alkoxysilane cluster compounds where R' is either derived from a primary alcohol or contains functionalities like fluoro groups, or both, is needed. The present invention, as described in detail below, provides a solution to this need.

Still further, the specific alkoxysilane cluster compounds disclosed in the examples in the above-noted U.S. patents only contained one R' species for each compound. Mixtures of different R' in the same alkoxysilane cluster compound have never been specifically disclosed before the present invention.

BRIEF SUMMARY OF THE INVENTION

Therefore, the present invention is directed to a process for preparing an alkoxysilane cluster compound of the formula:

$$RSi[SiO_4]_3[R']_{9-n}[R'']_n \quad (II)$$

wherein R is hydrogen, alkyl, alkenyl, aryl, or aralkyl; each R' is independently selected from alkyl, alkenyl, aryl or aralkyl with the proviso that at least a majority of R' radicals are sterically hindered alkyl groups having at least 3 carbon atoms; each R'' is selected from unsubstituted or functionally substituted alkyls, alkenyls, aryls or aralkyls, and polyoxyalkylene groups with the proviso that R'' radicals are different than R' radicals; and n is a number from 1 to 9, comprising reacting an alkoxysilane cluster compound of the formula:

$$RSi[SiO_4]_3[R']_9 \quad (IA)$$

wherein R and R' are as defined above, with an alcohol of the formula:

$$R''OH \quad (III)$$

wherein R'' is as defined above; in the presence of an effective amount of an acidic catalyst; employing at least about 0.8 n moles of said alcohol per one mole of said alkoxysilane cluster compound, wherein n is as defined above; and said reaction being carried out at about 60° C. to about 250° C.

Further, the present invention is also directed at alkoxysilane cluster compounds prepared by this process. These compounds are represented by the following formula:

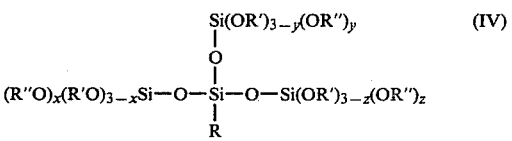

wherein R, R' and R'' are as defined above and x, y, and z are individually selected from 0, 1, 2, or 3 with the proviso that the sum of x+y+z is from 1 to 8.

Still further, the present invention is directed to the use of the alkoxysilane cluster compounds of formula (IV) in functional fluid systems (i.e., hydraulic fluid and heat transfer systems).

DETAILED DESCRIPTION

The improved method for preparing alkoxysilane cluster involves the reaction outlined in Equation A below between a previously made alkoxysilane cluster compound and an alcohol in the presence of an acidic catalyst:

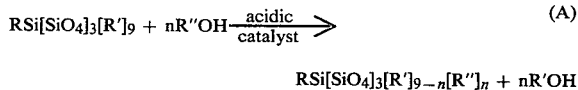

$$RSi[SiO_4]_3[R']_{9-n}[R'']_n + nR'OH$$

wherein R, R', R" and n are as defined above.

The alkoxysilane cluster reactants (represented by Formulae I and IA above) and the methods of their preparation are disclosed in U.S. Pat. Nos. 3,965,136 and 4,077,993. The utility of these reactants in functional fluid systems and in polyol compositions for rigid polyurethane foam production is shown in U.S. Pat. Nos. 4,048,084 and 4,147,849, respectively. The disclosures of these four patents are incorporated herein by reference in their entirety.

The preferred examples of these alkoxysilane cluster reactants include a R radical which is either hydrogen, an alkyl or an alkenyl having 1 to about 24 carbon atoms or an aryl or an aralkyl having from about 6 to about 24 carbon atoms. More preferably, R is either hydrogen, an alkyl or alkenyl group having 1 to about 8 carbon atoms or an aryl or aralkyl having about 6 to about 14 carbon atoms. Most preferably, R is either hydrogen or a lower alkyl group having 1 to 4 carbon atoms.

The preferred examples of these alkoxysilane cluster reactants also include R' radicals which are either alkyl or alkenyl groups having from 1 to about 24 carbon atoms or aryl or aralkyl groups having from about 6 to about 24 carbon atoms with the proviso that at least a majority of the R' radicals are sterically hindered alkyl groups having from 3 to about 24 carbon atoms. More preferably, all of the R' radicals of this reactant are sterically hindered alkyl groups having about 4 to about 12 carbon atoms. Most preferably, all of the R' radicals are sterically hindered alkyl groups derived from secondary or tertiary alcohols and having about 4 to about 12 carbon atoms. A specific example of the most preferred R' radical is a sec-butyl group.

Sterically hindered alkyl groups are defined as alkyl radicals which contribute to the hydrolytic stability of the molecule, i.e., which inhibit the reaction of water with the silicon-oxygen or the carbon-oxygen bonds in the molecule. Exemplary of preferred sterically hindered alkyl R' radicals include (1) non-linear primary alkyl radicals having a beta position side chain of at least 2 carbons, (2) secondary alkyl radicals, and (3) tertiary alkyl radicals. However, as mentioned above, it has now been found that cluster compounds containing the R' radicals of the latter two classes (e.g., sec-butyl) are somewhat easier to prepare than cluster compounds containing the non-linear primary alkyl radicals (e.g., iso-butyl, 2-ethyl butyl, 2-ethyl pentyl, 3-ethyl pentyl, 2-ethyl hexyl, 2,4-dimethyl-3-pentyl, and the like). Accordingly, the present invention may be particularly advantageous for making cluster compounds of the non-linear primary alkyl variety without having these preparation problems.

Accordingly, specific examples of the most preferred alkoxysilane cluster reactants for the method of the present invention include $CH_3Si[OSi(O-sec-butyl)_3]_3$ and $HSi[OSi(O-sec-butyl)_3]_3$.

The alcohol reactants R"OH of the present invention include any alcohol where the R" radical is an alkyl, alkenyl, aryl or aralkyl, a functionally substituted alkyl, alkenyl, aryl or aralkyl, or a polyoxyalkylene group, with the above-mentioned proviso that R" is different than R'. For example, if the alkoxysilane cluster reactant has a R' radical which is a secondary alkyl radical like sec-butyl, then it may be desirable to exhange some or all of these secondary alkyls with R" radicals (like 2-ethyl hexyl) which have higher molecular weights to improve thermal resistance, decrease volatility and improve lubricity of the cluster product.

In particular, it is an advantageous feature of the present invention to have the R" group be a sterically hindered non-linear alkyl group derived from primary alcohol in order to avoid the preparation and handling problems mentioned above when the R' radical is a non-linear primary alkyl radical.

Alternatively, it is also a desirable feature of the present invention to substitute or exhange some or all of R' radicals of cluster compound with R" radicals that contain functional groups therein. A functional group is defined as a group which is substantially unreactive to the other portions of the alkoxysilane cluster molecule, but provides the molecule with some beneficial property. For example, halo-substitutents on R" like fluoro groups may improve the fire-resistance properties of these alkoxysilane cluster compounds in functional fluids. Likewise, the presence of allyl or methylallyl groups may improve the lubricity properties of these cluster compounds in functional fluid systems. Further, polyoxyalkylene groups may be employed to either adjust the rubber swell properties of the cluster compound or change its surface tension properties for defoamer applications. Also, the presence of cyanoalkyl groups in the cluster compound may make the compound more compatable with nitrile rubbers and improve its di-electric properties.

The preferred examples of these alcohol reactants include a R" radical which is either an alkyl or an alkenyl group having from 1 to about 24 carbon atoms; an aryl or an aralkyl group having from about 6 to about 24 carbon atoms; alkoxy-, hydroxy-, halo-, or cyano-substituted alkyl or alkenyl group having from 1 to about 24 carbon atoms; alkoxy-, hydroxy-, halo-, or cyano-substituted aryl or aralkyl group having about 6 to about 24 carbon atoms; or polyoxyalkylene groups. More preferably, the R" radicals of this reactant are sterically hindered alkyl groups having 4 to about 24 carbon atoms; alkoxy-, hydroxy-, halo- or cyano-substituted alkyl or alkenyl having from 1 to about 12 carbon atoms; alkoxy-, hydroxy-, halo- or cyano-substituted aryl or aralkyl groups having about 6 to about 14 carbon atoms and polyoxyalkylene groups. The halo substitutents may independently be any halogen (i.e., F, Cl, Br or I). Dilhalo and trihalo compounds may also be used.

Specific examples of the more preferred R" radicals include sterically hindered non-linear primary alkyl such as iso-butyl, 2-ethyl butyl, 2-ethyl pentyl, 3-ethyl pentyl, 2-ethyl hexyl, and 2,4-dimethyl-3-pentyl; alkenyls such as allyl, methylallyl and 2-methyl-3-butenyl; aryls such as phenyl, ortho-tolyl, meta-tolyl, para-tolyl and xylyl; aralkyls such as benzyl and phenethyl; functionally substituted alkyls such as 2,3-dichloropropyl beta-hydroxyethyl, trifluoroethyl, trichloroethyl, trifluoropropyl, beta-cyanoethyl, 2,2-dichloro-3-hydroxypropyl; functionally substituted alkenyls such as 2-allyloxy-ethyl and 2-hydroxy-3-penteyl; functionally substituted aryls such as chlorophenyl, methoxyphenyl, hydroxyphenyl and dichlorophenyl; functionally substituted aralkyls such as chlorobenzyl and methoxybenzyl; and polyoxyalkylene groups such as polyoxyethylene methyl ether groups, polyoxyethylene ethyl ether groups and polyoxyethylene butyl ether groups and corresponding derivatives of propylene oxide, butylene oxide as well as mixtures of block or random structures of all three oxides.

In preparing the desired cluster products of formula (II), generally at least about 0.8 n to about 1.5 n moles of the alcohol R"OH are used per mole of the alkoxysilane cluster reactant of formula (I). Most preferably, about 1.0 n to about 1.2 n moles of the alcohol are used. Thus, if a complete exchange of R' radicals with R" radicals is exchanged, a theoretical minimum of 9 moles of R"OH should be used. If only a partial exchange is wanted then the number of moles of R"OH used will depend upon the number of R" radicals desired in the molecule.

Examples of products produced by the method of the present invention include compounds of the following formulae:

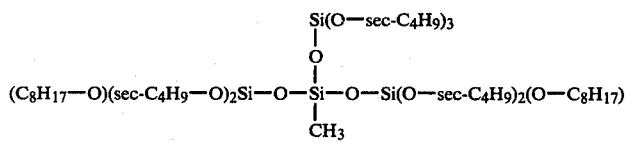
(V)

wherein R is methyl; R' is sec-butyl and 2 moles of 2-ethyl hexanyl (R") are exchanged for 2 moles of sec-butyl by the present reaction:

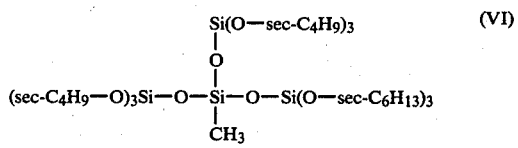
(VI)

wherein R is methyl; R' is sec-butyl; and 3 moles of 2-ethyl-butyl (R") are exchanged for 3 moles of sec-butyl by the present reaction. It appears that the exchange of R" for R' radicals is completely random and order of exchange is not yet known.

The reaction is performed in the presence of an acidic catalyst. The catalyst is necessary to cause the reaction rate to proceed at a reasonable rate. Without the catalyst, the reaction will occur at very slow rates. It should be noted that the present invention contemplates any acidic catalyst that will work; those which dissolve in the reaction mixture are preferred. Suitable acidic catalysts are p-toluol sulfonic acid, benzene-sulfonic acid, methane-sulfonic acid, phosphoric acid, sulfuric acid and trifluoroacetic acid. These are preferred over HCl, HBr, HI, since the latter are volatile and tend to form alkyl halides in the reaction mixture. P-toluol sulfonic acid is the most preferred catalyst because it does not char like $H_2SO_4$; it is a strong acid and more soluble than most acids in the reaction mixtures contemplated by the present invention.

Besides the acids mentioned above, the present invention contemplates the use of other forms of acidic catalysts such as Lewis acids, acidic ion-exchange resins and acidic alcohols. Examples of Lewis acids are listed in U.S. Pat. No. 3,976,675, which issued to Scott et al. on Aug. 24, 1976 and incorporated herein by reference in its entirety, and include boron trifluoride and its etherate derivatives, ferric chloride, ferrous chloride, stannic chloride, titanium, tetrachloride, hydrogen fluoride, aluminum bromide, triethyl aluminum zinc chloride, zinc bromide, tetrabutyl titanate, and so forth. Examples of acidic ion-exchange resins include sulfated polystyrene resins and the like. Examples of acidic alcohols include $CF_3CH_2OH$ and the like. In this latter case, the acidic alcohols may act as either a reactant or a catalyst. Also, acidic alcohols could be employed with other alcoholic reactants (R"OH) for their catalytic purposes only.

Any amount of catalyst which is catalytically effective may be employed. Generally, the concentration of the acid catalysts may range from about 0.1% to about 5.0%, and preferably, from about 1.0% to about 2.0% by weight of the alkoxysilane cluster reactant employed.

Reaction of Equation (A), above, may be carried out in the presence of a solvent but one is not necessary. A solvent may serve to moderate the rate of reaction and enhance the exchange of the R" radical for the R' radical. Any solvent may be used which dissolves the reactants and does not interfere with the reaction of Equation (A). Among the solvents which may be used are benzene, toluene, xylene, high boiling petroleum ether, other ethers such as tetrahydrofurane, and the like. The total amount of solvent used is a matter of choice and not critical to the reaction, although good results are achieved when about 20 moles to about 80 moles, and preferably about 40 to about 60 moles, of solvent are used per mole of alkoxysilane cluster reactant.

The reaction generally can be performed from moderate temperatures (e.g., about 60° C.) to very high temperatures (e.g., about 250° C.). Preferably, the reaction temperature of the present invention is from about 150° C. to about 200° C. When this reaction is carried out at atmospheric pressure, the most preferred temperature is generally around the boiling or reflux point of the alcohol R"OH.

Pressure is not believed to have any significant effect on this reaction, but superatmospheric or subatmospheric pressures are not prohibited from being employed. Generally, superatmospheric pressures of up to 100 atmospheres may be used. Such higher pressures may be advantageous when low boiling R'OH alcohols are being employed. Subatmospheric pressures down to about 0.05 mm Hg, preferably, in the range from about 400 to about 25 mm Hg, may be employed. Such low pressures may be advantageous to remove R'OH alcohols with an extremely high boiling point such as a fatty alcohol having about 10 to about 24 carbon atoms.

Any reaction time that is sufficient to obtain reasonable yields of the desired product may be used. Of course, the reaction time will depend on the nature of the R"OH employed, the reaction temperature and the nature of the catalyst and its concentration. Generally, reaction times from about 1 hour to about 30 hours, preferably about 5 hours to about 12 hours, may be used.

A preferred routine for conducting the reaction is to first charge the reaction vessel with the two reactants and the catalyst. The vessel is then blanketed with nitrogen to avoid oxidation and the reaction contents are stirred and heated to the desired reaction temperature for the desired time. While the reaction is being conducted, the alcohol R'OH being evolved is removed from the vessel to further drive the reaction. After completion of the reaction, the acid catalyst is removed by a water wash or neutralized by addition of an organic base, such as pyridine, triethylamine and the like, or an inorganic base, such as ammonia, $NaHCO_3$, $Na_2CO_3$, $K_2CO_3$, $CaO$, $Ca(OH)_2$, and the like. After neutralization, the resulting salts of the acid-base reaction are removed by suitable means, such as filtration, and any other impurities may be removed by distillation and the like.

During the neutralization of the acid catalyst, the minimum amount of base employed is generally dependent upon the amount of catalyst present. Preferably, a 5 to 20 molar excess of base over acid may be used with a solid base.

The novel alkoxysilane cluster compounds of the present invention as represented by Formula IV contain a sufficient number of silicon atoms so as to exhibit favorable lubricating properties. When both R' and R" are sterically hindered alkyl constituents, although different, the resulting compound will have good hydrolytic stability and an acceptable ASTM viscosity index. When R" contains a functional substituent (e.g., alkoxy, hydroxy, halo, allyl, or cyano group), the resulting compound may have improved properties which make the compound especially good for specialized functional fluid systems or other applications.

In some instances, it is practically impossible to separate the different novel compounds of the present invention because of their close boiling points, therefore, the present invention is intended to cover both these compounds singly and mixtures thereof and their use in functional fluid systems, both singly and in mixtures. The functional fluid systems to which the novel compounds of the present invention may be used include hydraulic-type functional fluid systems and heat transfer-type functional fluid systems.

The hydraulic-type fluid systems include any system wherein a mechanical effort is converted to pressure at a first location, the pressure is transmitted from this first location to a second location via a hydraulic fluid, and the pressure is converted to a second mechanical effort at the second location. Thus, the hydraulic systems contemplated by the present invention include hydraulic brake systems, hydraulic steering mechanisms, hydraulic transmissions, hydraulic jacks and hydraulic lifts. Included among these are the hydraulic systems used in heavy equipment and transportation vehicles including highway and construction equipment, railways, planes and aquatic vehicles. Also included are special or custom fluid-requiring systems such as high pressure or temperature gradient systems including those employed in arctic environments as well as those found in aerospace and lunar vehicles and the like.

The heat transfer-type fluid systems include the hydraulic systems described above wherein heat is dissipated by the hydraulic fluid and include many other systems as well. In general, the present invention contemplates heat transfer systems wherein heat is passed from a first heat conductor at a first location to a heat transfer fluid, the heat is transmitted from the first location to a second location via the heat transfer fluid, and the heat is passed from the heat transfer fluid to a second conductor at the second location. Thus, the heat transfer systems of the present invention include heat dissipation systems, fluidic heating systems (e.g., radiator-type circulating fluid heating systems), heat exchange systems such as gas-liquid and liquid-liquid concurrent and countercurrent tubular heat exchangers as are used for example, in the chemical process industries, cooling systems for nuclear reactors, radiator-type cooling systems, and any other temperature gradient systems in which a closed or sealed fluid heat transfer medium is used.

In the functional fluid systems of the present invention, the compounds of Formula IV, above, are used in an effective amount. In one embodiment, the compounds of Formula IV may be employed without additives or diluents. Alternatively, these compounds may comprise the base component of a functional fluid or may constitute a minor component, e.g., an additive, in a functional fluid containing a different base component. In general, an effective amount may be any amount which will produce the desired fluid characteristics for a given system. Therefore, as little as 5% by weight or less of one or more of the compounds of Formula IV may be used or as much as about 100% of the compounds may be used. For example, 20% to about 95% or about 100% of the functional fluid may be one or more of the compounds of Formula IV, e.g., 45 to 90% of the fluid may comprise one or more compounds of Formula IV.

Various diluents, inhibitors and other additives are well known in the functional fluid art and these may optionally be added to the functional fluids used in the systems of the present invention, if desired. For example, a diluent component may be one or more glycol monoethers of diethers such as diethylene glycol monoethyl ether, diethylene glycol monobutyl ether, triethylene glycol monomethyl ether, triethylene glycol monothyl ether, tetraethylene glycol monomethyl ether, ethylene glycol, propylene glycol, diethylene glycol and tetraethylene glycol. Various other diluents and mixtures thereof, which are well known in the art may also be used with the organosilane containing base component of this invention.

Generally, the particular amount of diluents which is used is not critical and widely varying amounts may be used. More particularly, the diluent components may constitute from 0% up to about 80% by weight of the fluid and preferably from about 20% to about 60%.

Various additives may be added to the fluids used in the systems of this invention to control or modify various chemical and physical properties. Among the various types of additives which can be added to the fluids are included inhibitors for pH and corrosion control, antioxidants, rust inhibitors, viscosity index improvers, pour point depressants, lubricating additives, antifoamants, stabilizers, vapor phase corrosion inhibitors, rubber swelling adjusters, demulsifiers, dyes and odor suppressants. Generally, the total amount of additives which may be incorporated into the fluid composition will vary between about 0% to about 20%, preferably from about 0.1% to 8% and more preferably from about 0.2% to about 5% by weight, based on the total weight of the fluid composition.

For example, alkaline inhibitors for pH and corrosion control may optionally be employed in an amount sufficient to maintain alkaline conditions in the fluid compositions, e.g. at an apparent pH value of from about 7 to about 11.5, if desired. These inhibitors may generally be added in an amount of from about 0% to about 8% by weight based on the total weight of fluid compositions, e.g., from about 0.5% to about 6%. Useful alkaline inhibitors include, for example, alkali metal salts of higher fatty acids such as potassium oleate, the potassium soap of rosin or tall oil fatty acids, amines such as morpholine and ethanolamine and amine salts such as mono- or dibutyl ammonium borates.

An antioxidant may optionally be used, if desired. Typical antioxidants include, 2,2-di-(4-hydroxyphenyl)-propane, phenothiazine, amines such as phenylalphanaphthylamine and hindered phenols such as dibutyl cresol. Generally, the amount of antioxidant used will vary from 0 to about 3% by weight, e.g., from about 0.001 to about 2% by weight based on the total weight of the fluid composition.

Additionally, other additives, if desired, may be incorporated into the fluid composition. For example, corrosion inhibitors such as butynediol and rubber swelling adjusters such as dodecyl benzene may be used.

The above-noted inhibitors and additives are merely exemplary and are not intended as an exclusive listing of the many well-known materials which can be added to fluid compositions to obtain various desired properties. Other illustrations of additives and diluents which may be used can be found in U.S. Pat. No. 3,377,288 and in "Introduction to Hydraulic Fluids" by Roger E. Hatton, Reinhold Publishing Corp. (1962).

The following examples depict preparation of the alkoxysilane cluster compounds of the present invention. All parts and percentages are by weight unless otherwise specified.

EXAMPLE 1

A one liter three neck flask was outfitted with a stirrer, thermometer and a 9" helix packed column of $\frac{3}{4}"$ diameter with a fractionation head.

The thermometer used to measure the pot temperature held the sensing head of a temperature controller to prevent overheating. The flask was charged with 101 g Cluster $H_3C$-Si[OSi(O-sec-$C_4H_9$)$_3$]$_3$ (0.121 moles), 1 g p-toluol-sulfonic acid as catalyst and 128 g 2-ethyl-1-butanol. This was 114% of the theoretically 111.5 g (1.09 moles) 2-ethyl-1-butanol needed to ensure complete exchange. The system was blanketed with $N_2$ to avoid oxidation and the contents were heated to 150° C. with the maximum temperature set at 190° C. The sec-butanol generated was slowly taken off using an approximate reflux ratio of 30:1. Within 8 hours, 78.3 g of a mixture, boiling between 98° and 120° C. with the pot at 190° C. were collected. Theoretically, 80.8 g sec-butanol should have been distilled. To drive the reaction further, 135 g more 2-ethyl-1-butanol was added and the heating was continued for 4 more hours. 109.7 g distillate was recovered. A V.P.C. analysis of it showed that it consisted of 62% sec-butanol and the rest 2-ethyl-1-butanol. Thus 68.11 g sec-butanol was recovered, which was 84.2% of theory. The mixture was cooled, mixed with 200 ml toluene and was water-washed 2 times with 200 ml aqueous solution containing 5% $NaHCO_3$ and 3 times with 200 ml water to remove the acid catalyst. The solution was then dried with 50 g $MgSO_4$. After filtration, solvent stripping and removal of any remaining 2-ethyl-1-butanol by vacuum distillation the product was purified by molecular distillation. After forecuts were taken between 90° and 140° C. evaporator temperature ($10^{-3}$ mm Hg) we obtained 30.9 g of a distillate evaporating at 150°-180° C. ($10^{-3}$ to $5\times 10^{-4}$ mm Hg) (Fraction I, while 71.3 g distill in 2 passes at 210° C.) ($10^{-3}$ to $10^{-4}$ mm Hg) (Fraction II). Both fractions contained mixtures of alkoxysilane cluster products of this invention which may be resolved by V.P.C.

Specifically, the following distribution was obtained:

| No. of 2-ethylbutyl groups in Cluster | wt % Fraction I | wt % Fraction II |
|---|---|---|
| 9 | 23.14 | 59.70 |
| 8 | 18.06 | 25.74 |
| 7 | 14.90 | 12.69 |
| 6 | 11.53 | N.D.* |
| 5 | 11.27 | N.D.* |
| 4 | 8.71 | N.D.* |
| 3 | 9.10 | N.D.* |
| 2 | 1.36 | N.D.* |
| 1 | N.D.* | N.D.* |
| 0 (all sec-butyl group left on the cluster) | 0.79 | N.D.* |

*N.D. means not detected

EXAMPLE 2

The experimental set-up identical to that of Example 1 was repeated and a 2 liter flask was employed. 323.3 g Cluster $H_3C$-Si[OSi(O-sec-$C_4H_9$)$_3$]$_3$ (0.388 moles), 3.5 g p-toluol-sulfonic acid and 461 g 2-ethyl-1-hexanol (3.54 moles) were charged and the reaction started at 167° C. with maximum temperature set at 190° C., 197 g sec-butanol was collected in 12 hrs., bp 94°-98° C. To complete the reaction another 61 g 2-ethyl-1-hexanol (0.468 moles) was added and the reaction continued for 5 more hrs. at 180°-190° C. A total of 210.1 g sec-butanol with a refractive index $n_D^{20}=1.3973$ (literature value for sec-butanol is $n_D^{20}=1.3971$) was collected, which represented a 81.2% theoretical conversion. To neutralize the acid catalyst, the reaction mixture was stirred 1 hr. starting at 60° C. with 16 g Ca(OH)$_2$. The calcium salts were filtered through filter aid, excess 2-ethyl-1-hexanol was vacuum distilled to a pot temperature of 190° C./0.05 mm Hg. A final purification of the high boiling material was done in a falling film molecular still with continuous recycle of undistilled material.

Low boiling materials collected in an amount of 63.8 g at a heater temperature of 157° at $5\times 10^{-2}$ to $10^{-3}$ mm Hg. 384 g main product was collected at 250° C. and $5\times 10^{-4}$ to $10^{-4}$ mm Hg.

The material in the main product could not be assayed by V.P.C. because the boiling points of these alkoxysilane cluster products were too high to give sharp and separate peaks. Instead, the V.P.C. analysis showed broad overlapping peaks. However, the formation of the desired product was also strongly evidenced by the evolution of the sec-butanol during the reaction.

EXAMPLE 3

The experiment of Example 1 was again repeated but the following reagents and quantities are changed:

$H_3C$—Si[OSi(O—sec-$C_4H_9$)$_3$]$_3$    178 g (0.213 mole)

| | |
|---|---|
| -continued | |
| p-toluol sulfonic acid | 2.5 g |
| dipropylene glycol monomethyl ether | 329 g, (2.22 moles) or 115.8% of theory for complete exchange. |

Heating was carried out for 15 hrs. from 170°-190° C. afforded 103.8 sec-butanol with a refractive index $n_D^{20}=1.3974$. This corresponded to 72.8% conversion. The brown reaction product was neutralized with 15 g $Ca(OH)_2$ to which 3 g active carbon was added to bind the color. The filtered yellow crude product was then vacuum stripped from unreacted dipropylene glycol and monomethyl ether before being distilled in a falling film molecular still. Low boilers are removed at 150° C. ($5 \times 10^{-3}$ to $10^{-4}$ m) (24 g) followed by 137.7 g main product at 234°-260° C. ($5 \times 10^{-3}$–$10^{-4}$ mm Hg). 34.9 g material is undistillable.

The product was not resolved by V.P.C. for the same reasons as stated in Example 2.

EXAMPLE 4

A 2 liter flask was equipped with a magnetic stirrer and a fractionation head, which acted as a reflux condenser. 814 g Cluster $H_3C—Si[OSi(O\text{-sec-}C_4H_9)_3]_3$ (0.977 moles), 5 g p-toluol-sulfonic acid and 216 g allyl alcohol (3.72 moles) was added. The flask was blanketed with $N_2$ and the contents were refluxed for 5 hrs. A receiving flask was attached and the sec-butanol/allyl alcohol mixture was then distilled off. (No separation is possible since the bp is 98° for sec-butanol and 96°-98° for allyl alcohol). We obtained 98.4 g of a mixture, which has a refractive index $n_D^{20}=1.4024$, indicating 59 mole % sec-butanol and 41 mole % allyl alcohol. At this point, 100 g (1.72 moles) more allyl alcohol was added and the refluxing was continued for 6 more hrs. 20 g $(Ca(OH)_2)$ and 5 g active carbon were added to neutralize the catalyst and remove a discoloration. The solids were removed by filtration and the allyl alcohol/butanol was stripped of a rotary evaporator. Last traces of solvent were removed at 100° C. and 0.05 mm Hg overnight.

709 g crude product was obtained.

The approximate species distribution was ascertained by V.P.C. analysis.

| No. allyl groups in cluster | % by weight in product |
|---|---|
| 0 (original cluster reactant) | 22.4 |
| 1 | 15.2 |
| 2 | 11.5 |
| 3 | 10.1 |
| 4 | 9.2 |
| 5 | 8.9 |
| 6 | 9.3 |
| | 86.6 |

Balance (13.4%) unidentified low molecular weight species.

NMR analysis indicated the following ratios in the overall mixture:
OSi-sec-butyl/Si—$CH_3=6.5$
allyl/Si—$CH_3=2.5$
sec-butyl/allyl$=2.6$

EXAMPLE 5

Example 4 was repeated in a 3 liter flask, but 491 g Cluster $H_3C—Si[OSi(O\text{-sec-}C_4H_9)_3]_3$ (1.13 mole), 1209 g allyl alcohol (20.82 moles) and 4.5 g p-toluol sulfonic acid were refluxed for 15 hrs. After neutralization with 20 g $Ca(OH)_2$ and 5 g active C the filtered solution was stripped from the alcohols on a rotary evaporator. The refractive index of the alcohol mixture is 1.4047 which corresponded to 52.56 mole % allyl alcohol and 47.44 mole % sec-butanol. To clear a yellowish turbidity, 5 g Attaclay and 3 g active carbon were added, the mixture was then stirred 30 minutes and filtered.

764 g clear filtrate was obtained.

The V.P.C. analysis showed the following species distribution:

| No. allyl groups in cluster | % by weight |
|---|---|
| 0 (original reactant) | 2.26 |
| 1 | 2.08 |
| 2 | 2.52 |
| 3 | 3.72 |
| 4 | 6.21 |
| 5 | 10.69 |
| 6 | 14.37 |
| 7 | 31.67 |
| 8 | 12.59 |
| 9 | 5.58 |
| | 91.69 |

The difference to 100% were cleavage and other unidentified by-products.

NMR analysis showed the following ratios in the crude mixture:
sec-butanol/Si—$CH_3=3.7$
allyl/Si—$CH_3=6.4$
allyl/sec-butyl$=1.7$ The products obtained from the above examples were tested for viscosity, wear scar, flash point and weight loss as shown in the following Table I. The wear scar test was performed with a four ball 40 Kg load apparatus at 1800 rpm and 168° F. for 1 hour. The results established that the novel compounds of the present invention are very good functional fluids.

TABLE I

| | Example 1 | Example 2 | Example 3 | Example 5 |
|---|---|---|---|---|
| Viscosity 100° F. (cst) | 31.33 | 32.39 | 20.99 | 6.65 |
| Viscosity 210° F. (cst) | 9.81 | 10.20 | 5.70 | 2.79 |
| Viscosity —40° F. (cst) | 866.2 | 891.0 | 2514.9 | 66.5 |
| Viscosity —65° F. (cst) | 2815.1 | 2985.6 | 16533 | 148.6 |
| Extended Viscosity Index* | 399 | 342 | 254 | 403 |
| Wear Scar (4 Ball) 1200 RPM, 40 kg 167° F., 1 hour | 0.91 mm | 0.65 mm | 1.42 mm | 0.89 mm |
| Flash Point °F. (Setaflash) | 380 434** | 368 420** | N.D. 318** | N.D. 278** |
| Weight loss % 1 hour at 400° F. (1 g in dish of 2 in diameter) | 1.42% | 1.20% | 3% | 30.6% |

*calculated according to ASTM D2270
**With Inhibitor (1% by weight Irganox LO6 added to the product)
N.D. means not determined

What is claimed is:

1. A process for preparing an alkoxysilane cluster compound of the formula:

$$RSi[SiO_4]_3[R']_{9-n}[R'']_n$$

wherein R is hydrogen, alkyl, alkenyl, aryl or aralkyl; each R' is independently selected from alkyl, alkenyl, aryl or aralkyl with the proviso that at least a majority of R' radicals are sterically hindered alkyl groups having at least 3 carbon atoms; each R" is selected from alkyl, alkenyl, aryl or aralkyl, functionally substituted alkyls, alkenyls, aryl or aralkyls; and polyoxyalkylene groups with the proviso that R" radicals are different than R' radicals; and n is a number from 1 to 9;

comprising reacting an alkoxysilane cluster compound of the formula:

RSi[SiO$_4$]$_3$[R']$_9$ wherein R and R' are as defined above, with an alcohol of the formula:

R"OH wherein R" is as defined above;
in the presence of an effective amount of acidic catalyst;
employing at least about 0.8 n moles of said alcohol per one mole of said alkoxysilane cluster compound wherein n is defined above;
and said reaction being carried out at about 60° C. to about 250° C.

2. The process of claim 1 wherein about 0.9 n to about 1.5 n moles of said alcohol R"OH are used per mole of said alkoxysilane cluster reactant.

3. The process of claim 1 wherein said reaction temperature is in the range from about 150° C. to about 200° C.

4. The process of claim 1 wherein about 1.0 n to about 1.2 n moles of said R"OH alcohol per mole of said alkoxysilane cluster reactants.

5. The process of claim 1 wherein a complete exchange of R" radicals for R' radicals occurs.

6. The process of claim 1 wherein said acidic catalyst is selected from the group consisting of p-toluol sulfonic acid, sulfonic acid, methane-sulfonic acid, phosphoric acid, sulfuric acid and trifluoroacetic acid.

7. The process of claim 6 wherein said acidic catalyst is p-toluol sulfonic acid.

8. The process of claim 1 wherein said R radical is either hydrogen, an alkyl or alkenyl group having 1 to about 8 carbon atoms or an aryl or aralkyl group having about 6 to about 14 carbon atoms and said R' radicals are all sterically hindered alkyl groups derived from secondary or tertiary alcohols and having from about 4 to about 12 carbon atoms.

9. The process of claim 8 wherein said R" radicals are either sterically hindered alkyl groups having 4 to about 24 carbon atoms; alkoxy- hydroxy-, halo-, or cyano-substituted alkyl or alkenyl groups having from 1 to about 12 carbon atoms; alkoxy-, hydroxy-, halo-, or cyano-substituted aryl or aralkyl groups having from about 6 to about 14 carbon atoms, or polyoxyethylene groups.

10. The process of claim 9 wherein about 0.9 n to about 1.5 n moles of said alcohol R"OH are used per mole of said alkoxysilane cluster reactant.

11. The process of claim 10 wherein said acidic catalyst is selected from the group consisting of p-toluol sulfonic acid, sulfonic acid, methane-sulfonic acid, phosphoric acid, sulfuric acid and trifluoroacetic acid.

12. The process of claim 11 wherein said R radical is either hydrogen or a lower alkyl group having 1 to 4 carbon atoms.

13. The process of claim 12 wherein said R' is sec-butyl group.

14. The process of claim 13 wherein said R" radical is a sterically hindered non-linear alkyl group derived from a primary alcohol.

15. The process of claim 14 wherein a complete exchange of R" for R' radicals occurs.

16. The process of claim 15 wherein said reaction temperature is in the range from about 150° C. to about 200° C.

17. An alkoxysilane cluster compound of the formula:

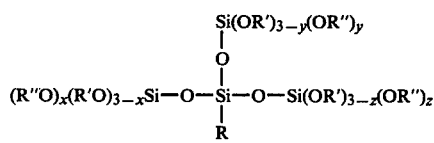

wherein R is hydrogen, alkyl, alkenyl, aryl or aralkyl; each R' is independently selected from alkyls, alkenyls, or aryls or aralkyls with the proviso that at least a majority of R' radicals are sterically hindered alkyl groups having at least 3 carbon atoms; each R" is selected from alkoxy-, hydroxy-, halo-, or cyano-substituted alkyl or alkenyl groups having from 1 to about 12 carbon atoms; alkoxy-, hydroxy-, halo-, or cyano-substituted aryl or aralkyl groups having 6 to about 14 carbon atoms; or polyoxyethylene groups; and x, y, and z are individually selected from 0, 1, 2, and 3 with the proviso that the sum of x+y+z is from 1 to 8.

18. In a method wherein a first mechanical effort is converted to pressure at a first location, the pressure is transmitted from said first location to a second location via a hydraulic fluid, and said pressure is converted to a second mechanical effect at said second location, the improvement which comprises using as said hydraulic fluid one which comprises an effective amount of a compound having the formula:

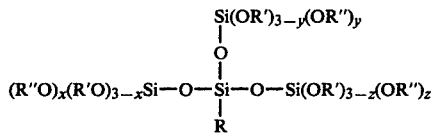

wherein R is hydrogen, alkyl, alkenyl, aryl or aralkyl; each R' is independently selected from alkyls, alkenyls, aryls or aralkyls with the proviso that at least a majority of R' radicals are sterically hindered alkyl groups having at least 3 carbon atoms; each R" is selected from alkoxy-, hydroxy-, halo-, or cyano-substituted alkyl or alkenyl groups having from 1 to about 12 carbon atoms; alkoxy-, hydroxy-, halo-, or cyano-substituted aryl or aralkyl groups having about 6 to about 14 carbon atoms; or polyoxyethylene groups; and x, y, and z are individually selected from 0, 1, 2, and 3 with the proviso that the sum of x+y+z is from 1 to 8.

19. In a method wherein heat is passed from a first heat conductor to a heat transfer fluid at a first location, the heat is transmitted from said first location to a second location via said heat transfer fluid, and said heat is passed to a second heat conductor at said second location; the improvement which comprises using as said heat transfer fluid one which comprises an effective amount of a compound having the formula:

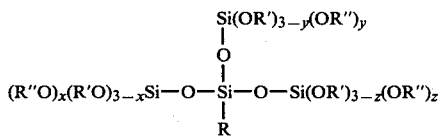

wherein R is hydrogen, alkyl, alkenyl, aryl or aralkyl; each R' is independently selected from alkyls, alkenyls, aryls or aralkyls with the proviso that at least a majority of R' radicals are sterically hindered alkyl groups having at least 3 carbon atoms; each R" is selected from alkoxy-, hydroxy-, halo-, or cyano-substituted alkyl or alkenyl groups having from 1 to about 12 carbon atoms; alkoxy-, hydroxy-, halo-, or cyano-substituted aryl or aralkyl groups having about 6 to about 14 carbon atoms; or polyoxyethylene groups; and x, y, and z are individually selected from 0, 1, 2, and 3 with the proviso that the sum of x+y+z is from 1 to 8.

* * * * *